United States Patent [19]

Rebhan

[11] Patent Number: 4,931,290

[45] Date of Patent: Jun. 5, 1990

[54] MILK FEVER PROPHYLACTIC TREATMENT AND COMPOSITION

[75] Inventor: Herbert J. Rebhan, New Richmond, Wis.

[73] Assignee: Domain, Inc., New Richmond, Wis.

[21] Appl. No.: 248,994

[22] Filed: Sep. 23, 1988

[51] Int. Cl.$^5$ .................... A61K 33/08; A61K 33/06; A61K 31/19

[52] U.S. Cl. .................... 424/692; 424/639; 424/600; 424/641; 424/643; 424/647; 424/648; 424/678; 424/682; 424/690; 424/691; 424/698; 514/167; 514/557; 514/574

[58] Field of Search .............. 424/692, 696, 698, 639, 424/600, 641, 643, 647, 648, 678, 682, 690, 691; 514/557, 167, 574

[56] References Cited

PUBLICATIONS

Gerloff et al., "Dry Cow Feeding and Metabolic Problems", 46th Minnesota Nutrition Conference and Monsanto Technical Symposium, Minnesota Agricultural Extension Service, pp. 30–46 (1985).

Goff et al., "Use of 24-F-1, 25-Dihydroxyvitamin $D_3$ to Prevent Parturient Paresis in Dairy Cows", ADSA Journal Dairy Science, vol. 71, No. 5, May 1988.

Aseltine, "Overfeeding of Vitamins to Dairy Animals can be Harmful", Nutrition & Health, Feedstuffs, May 23, 1988.

Ringarp et al., Jul. 1966 (German). Vorbengende Bohandlung der Puerperalparesis mit Kuzumchlorid (Versuch Nr. II).

Jorgensen, "Combating Milk Fever", Journal of Dairy Science, vol. 57, No. 8, pp. 933–944 (American Dairy Science Association Symposium, Pullman, Washington, Jun. 26, 1973.

McFadzen et al., "Parturient Paresis", Current Veterinary Therapy, Food Animal Practice, W. B. Saunders Company, 1981, pp. 340–343.

Dukes et al., "The Physiology of Domestic Animals", Comstock Publishing Associates, New York, 1955, pp. 376–381.

Conrad et al., "Studies on Milk Fever in Dairy Cows V. the Effect of Massive Oral Doses of Vitamin D on Absorption, Excretion, Retention and Blood Levels of Calcium and Phosphorus", Department of Dairy Science, Ohio Agricultural Experiment Station, pp. 1697–1705 (1956).

*Primary Examiner*—Frederick E. Waddell
*Attorney, Agent, or Firm*—James R. Haller; Gregory P. Kaihoi; Mary P. Bauman

[57] ABSTRACT

A method is disclosed for reducing the propensity of a dairy cow to develop severe milk fever upon calving comprising administering thereto a composition comprising a water-soluble calcium compound and a complexing agent for serum phosphorus.

24 Claims, No Drawings

MILK FEVER PROPHYLACTIC TREATMENT AND COMPOSITION

BACKGROUND OF THE INVENTION

Upon calving, dairy cows begin to produce large quantities of milk, leading to heavy drains upon serum calcium levels. Very low serum calcium levels can cause death of dairy cows within hours or days of calving, and this condition is referred to as "milk fever". Approximately one-fifth of dairy cows suffer milk fever to some extent upon calving, and with jersey cows, this fraction is closer to four-fifths.

Serum calcium commonly is provided by calcium-containing foods. Calcium is stored in the bones of cows, and the bones commonly supply calcium to replenish badly depleted levels of serum calcium. The ease with which calcium stored in the bones passes into the blood serum, and vice versa, appears to decrease with the age of the cows and also appears to be particularly poor in jersey cows.

A number of methods have been proposed in an attempt to reduce the incidence of milk fever in cows. Gerloff, et al., "Dry Cow Feeding and Metabolic Problems", 46th Minnesota Nutritional Conference and Monsanto Technical Symposium, September 16–18, 1985 suggests that excessive calcium and phosphorus intake should be avoided prior to calving in an effort to prevent "PP" (parturient paresis, a synonym for milk fever). The authors state that, "Very low calcium intakes (<20 g daily) are effective in preventing PP and may be fed for the last two weeks prepartum." A summary of procedures for combatting milk fever are discussed in Jorgensen, N. A., "Combatting Milk Fever", Journal of Dairy Science, Vol. 57, No. 8, 1973, pp. 933–944. Methods of combating milk fever included feeding prepartal diets low in calcium, adjusting the dietary calcium-to-phosphorus ratio, feeding acidic diets, mineral acids, or ammonium chloride prepartum, short term administration of 90 to 100 g. of calcium chloride daily, feeding massive doses of vitamin D prepartum, and prepartum administration of 25-hydroxy-cholecalciferol. The intravenous administration of calcium salts is recommended as a treatment for severe milk fever, and is reported in Howard, Ed., "Current Veterinary Therapy I: Food Animal Practice", W. B. Saunders Co., Philadelphia, 1981, pp. 340–343. This text mentions the administration of vitamin D2 and of a vitamin D3 metabolite ante partum to reduce the incidence of milk fever. Also mentioned is the administration of 90 to 100 grams of calcium chloride orally for two to three days ante partum to two to three days postpartum to reduce incidence of the disease.

Notwithstanding the treatments suggested above, milk fever remains an extremely serious disease that affects postpartum dairy cows. A simple, safe and effective procedure for avoiding the onset of severe milk fever is much to be desired.

SUMMARY OF THE INVENTION

It has been found that the administration of effective quantities of a soluble calcium compound and a phosphorous complexing compound immediately after calving and also at least from about every 8 to about 16 hours thereafter for at least three consecutive dosages within about the first 30 hours after calving substantially reduce the severity of milk fever in dairy cows. The combination of ingredients can be administered separately, but much more conveniently is provided in the form of a unit dosage which is dissolved in water and is administered in a drenching operation.

Thus, in one embodiment, the invention relates to a method for treating postpartum dairy cows to reduce the propensity of the cows to develop severe milk fever. The method comprises orally administering to a cow immediately after calving and from at least about every 8 to 16 hours thereafter for at least three consecutive administrations within about 30 hours after calving, , an effective quantity of a water-soluble calcium compound (desirably providing at least about 40 grams and preferably at least about 75 grams of calcium), and an effective quantity of a compound capable of forming a water-insoluble complex with phosphorus, the latter compound desirably being present in an amount providing at least about 8 and preferably at least about 17 grams of magnesium or its equivalent. The water-soluble calcium salt preferably is the salt of an organic acid, desirably acetic or propionic acid, and the compound capable of forming a water insoluble complex with serum phosphorus is preferably an oxide, hydroxide or salt of magnesium, iron, manganese, zinc, aluminum or chromium, and most preferably is magnesium sulfate, magnesium oxide or magnesium acetate.

The complexing agent and the water-soluble calcium compound can be provided as a prepared unit dosage composition, preferably as a powdered, water-reducible and desirably water-soluble solid. Accordingly, the invention in another embodiment provides a method for treating postpartum cows to reduce the severity of milk fever in which the cows are orally drenched immediately after calving and from at least about 8 to 16 hours thereafter for a total of at least about 3 dosages, in the first 30 hours after calving with a unit dose composition comprising an effective quantity of a water-soluble calcium compound and an effective quantity of a complexing agent capable of forming a water-insoluble complex with phosphorus, the calcium compound and complexing agent being present desirably in amounts providing at least about 40 grams of calcium and at least about 8 grams of magnesium or its equivalent, respectively, per dosage.

In yet another embodiment, the invention relates to a medicinal composition in unit dosage form that can be orally administered to dairy cows postpartum to reduce the incidence of severe milk fever. The composition comprises the above-mentioned water-soluble calcium salt and phosphorus complexing agent, both desirably in the form of dry, water-reducible powders which can be taken up in water for oral administration to dairy cows.

The dosages referred to above desirably also include Vitamin $D_3$, each dosage including preferably at least 20,000 USP units of Vitamin $D_3$.

DESCRIPTION OF THE PREFERRED EMBODIMENTS

By administering to postpartum cows effective quantities of water-soluble calcium salt and a complexing agent capable of forming a water-insoluble complex with serum phosphorus, we have found it possible generally to maintain serum calcium at levels which avoid severe milk fever. Preferably, the calcium compound and the complexing agent are orally administered to dairy cows beginning immediately after calving and are also given at least from about every 8 to 16 hour period after calving. Desirably, the dosage is orally administered immediately after calving and then approximately every 12 hours after calving. It may be desirable to administer two dosages immediately after calving. Of importance, the first dosage should be given as soon after calving as possible, preferably in the first hour or two following calving. It is recognized that a dairy farmer may in some instances not be aware that a cow has calved until a matter of hours after the event has occurred, and "immediately after calving", as used here, is meant to include a reasonably short period which may extend through several hours after calving. The effectiveness of the milk fever prophylactic treatment described herein depends in part upon administering the first dose to a cow as soon as possible after calving to avoid extreme drops in serum calcium levels after calving has occurred. The 8 to 16 hour periods following calving are approximate time periods during which subsequent dosages should be administered to a cow in order to prevent serum calcium levels from drastically decreasing during the first few days following calving. As mentioned above, consecutive doses are desirably spaced about 12 hours apart, but from a practical standpoint, the period between dosages may be shortened or lengthened as may be necessary to fit the dairy farmer's schedule.

The first few days following calving appear to be most critical from the standpoint of development of milk fever. In accordance with the invention, at least three and preferably at least 6 consecutive dosages of the milk fever prophylactic composition described herein should be administered, the first three doses being given within about the first 30 hours after calving. A typical administration schedule may involve a first dosage administration immediately upon calving, as discussed above, with subsequent dosage administrations occurring after 12, 24, 36, 48, and 72 hours. The last two dosages, and particularly the last dosage, are of lesser importance since, by the third day following calving, serum calcium levels normally are on the increase toward standard levels. Further, as pointed out below, the quantity of water-soluble calcium salt that is administered may be reduced during the later stages of treatment. For example, the amount of soluble calcium salt administered in the fourth dosage may be half that administered in the first dosage.

The water-soluble calcium compound that is employed in the present invention desirably is a calcium salt and preferably a salt of a monobasic organic acid such as acetic acid and propionic acid. Other calcium compounds that may be employed include calcium chloride, calcium citrate and calcium borogluconate. Calcium acetate is particularly preferred since the presence of the acetate ion seems to help cows return to full feed more quickly. There is generally a drop in feed consumption following calving, and the acetate ion appears to lessen the feed consumption drop. Also, since acetic acid is the major organic acid constituent in the rumen, the addition of acetate ion to the rumen is not likely to cause any problems. The calcium compound, in any event, desirably is provided in the form of a dry powder which is readily dissolved in water.

The initial dosage orally administered to a cow immediately after calving should contain a sufficient amount of the calcium compound to provide calcium, expressed as elemental calcium, of not less than about 40 grams and preferably at least about 75 grams. 40 grams of elemental calcium corresponds roughly to 150 grams of calcium acetate, and 75 grams of elemental calcium corresponds to approximately 300 grams of calcium acetate. Preferably, at least the first dosage that is administered, and desirably the first two or three dosages, contain at least about 75 grams of calcium in the form of a water-soluble calcium compound. The level of calcium can, if desired, be reduced in subsequent dosages, and the fourth dosage, for example, may contain not more than about 40 grams of calcium in the form of a water-soluble calcium compound. Desirably, however, each dosage contains at least about 75 grams of calcium as the water-soluble calcium compound; by providing unit dosages with constant amounts of calcium, storage and inventory problems are reduced, as is any confusion over dosage amounts. Also, although I do not wish to be bound by the following explanation, I theorize that the administration of large quantities of calcium (at least about 75 grams in each approximately 8-hour period) may tend to tie up some of the phosphorus in the cow's diet or, broadly speaking, render the phosphorus nutritionally unavailable to the cow. The reduction in diet phosphorus contributes to the reduction of serum phosphorus levels, and this, I theorize, may signal the cow's system to take calcium and phosphorus out of the bone; calcium from the bone, together with calcium resulting from the orally administered water-insoluble compound, contributes to an increase in serum calcium levels.

The phosphorous complexing agent is capable of forming, with serum phosphorus, an insoluble complex which is eventually eliminated from the system of the cow. It is believed that the complexing agent thus reduces the level of serum phosphorus and that this in turn enables the serum calcium level to be maintained at a safe level through administration of a water-insoluble calcium compound such as calcium acetate. Complexing agents for serum phosphorus include the oxides, hydroxides and salts of magnesium, iron, manganese, zinc, aluminum and chromium. Magnesium compounds are preferred, and magnesium sulfate, magnesium acetate and magnesium oxide and mixtures thereof (especially magnesium sulfate and magnesium acetate mixtures) are particularly preferred. The amount of phosphorus complexing agent that is administered in each dose during the course of the treatment preferably provides at least 8 grams of magnesium or its equivalent (chemical equivalent) and preferably at least about 17 grams of magnesium or its equivalent, corresponding, respectively, to about 13 grams and about 28 grams of magnesium oxide, respectively. It will be understood that, when added to water, magnesium oxide forms the hydroxide which is substantially insoluble. Magnesium oxide is commercially available as a very fine powder which is readily dispersed in water to make a drench. Magnesium acetate and magnesium sulfate, on the other hand, are readily soluble in water. Whereas magnesium oxide (or hydroxide) in water slowly settles, requiring a drench preparation to be stirred just before administration, use of a water-soluble magnesium salt, preferably the sulfate or the salt of a lower monobasic acid such as acetic or propionic acid, and results in a solution which can be stored if need be and then administered without stirring.

Magnesium is said to be essential in several animal enzyme systems, and many enzymes require $Mg++$ in addition to ATP for their activity, reference here being made to Harrow, B. and Mazur, A., *Textbook of Biochemistry*, sixth edition, W. B. Saunders Company, Philadelphia, 1954, p. 305. Also, intraveneously administered magnesium may help resolve "alert downer syndrome" in which cows are unable to rise but are otherwise alert, reference being made to Howard, J. L., ed., *Current Veterinary Therapy*, W. B. Saunders Company, Philadelphia, pp. 353-355.

Preferably, there is also orally, preferably concurrently, administered to postpartum cows immediately after calving and also from about every 8 to 16 hours thereafter for at least three consecutive administrations in the first 30 hours after calving an effective quantity of Vitamin $D_3$, preferably in an amount of at least 20,000 USP units and most preferably at least 40,000 USP units. Vitamin $D_3$ is commercially available as a water-dispersible, substantially water-insoluble powder that is storage stable at the neutral or slightly alkaline pHs achieved with calcium and magnesium acetates. A dye may be incorporated with the vitamin $D_3$ or with the other ingredients referred to above so as to provide a distinctive color to an aqueous solution or suspension of the ingredients.

The water-soluble calcium compound, complexing agent such as magnesium acetate and/or magnesium sulfate, and optionally Vitamin $D_3$, may be administered separately to postpartum cows, or, more conveniently, may be administered together in a single treatment. Preferably, however, the ingredients are provided in the form of dry powders which are combined and packaged, each package containing the desired quantities of these ingredients. The unit dose packages may be provided in any convenient form. Confinement of the unit dose ingredients in sealed plastic bags is preferred, but it is contemplated that the ingredients may be provided in the form of tablets, gelatin, capsules, boluses or the like. To administer the unit dose composition in packaged, powdered form to a cow, the package contents may simply be stirred into cold water, whereupon the calcium compound and any other soluble compounds dissolve and the complexing agent, if substantially water-insoluble as MgO, forms a suspension together with vitamin $D_3$, if present. The resulting liquid can be forced down the throat of a cow by known "drenching" procedures. The composition may also be sprinkled on or combined with feed such as hay.

As background against which the following examples may be more readily understood, milk fever generally proceeds in three stages. In stage I (sometimes referred to as "standing milk fever"), the cow is capable of standing and may be atoxic or show hind leg stiffness, although temperature and other vital signs may be normal. The normal concentration of blood serum calcium is about 9.4 mg/DL. The concentration of serum calcium for a stage I cow may be on the order of 6.2±1.3 mg/DL. As the cow progresses to stage II, it becomes recumbent with slow, shallow and irregular respirations and a reduced intensity of heart sounds. Stage II serum calcium concentration is generally approximately 5.5±1.3 mg/DL. In stage III, the cow will become comatose with sub-normal temperature, often elevated heart rate, and slow, shallow and irregular respirations. The pupils are dilated, and bloating may occur. Stage III calcium levels may be approximately 4.6±1.1 mg/DL. Cows entering stage III may die with or without treatment (such as intravenous administration of calcium), and may incur muscle damage and may not be able to get up again.

The following non-limiting examples are provided for illustrative purposes only. The day of calving is day #1.

EXAMPLE I

Prepackaged compositions may be produced by combining calcium acetate, magnesium oxide and magnesium sulfate (in equal amounts by weight), and optionally vitamin $D_3$ in powdered form, and then dividing the resulting material into aliquots in which each aliquot contains 300 grams of calcium acetate and sufficient quantities of the magnesium compounds to provide 17 grams of magnesium. The aliquots are packaged in plastic film envelopes which may be sealed by known heat-sealing means. Each packet containing a unit dosage of the prophylactic composition of the invention may be broken open and stirred into a liter of water to provide a composition suitable for drenching. 20,000 USP units of Vitamin $D_3$ may be incorporated in each packet.

EXAMPLE II

Six cows (2 jerseys and 4 holsteins) having no history of milk fever were tested on the day of calving and during each of the following four days to determine serum calcium and phosphorus levels. No prophylactic treatment was administered to these cows. Serum calcium and phosphorus levels are reported in the following table, the cows being identified as "no history, no treatment". A second group of five cows, each having had a history of milk fever during prior calvings, were treated on the day of calving and on each of the succeeding four days with dosages of a composition of the invention containing 150 grams of calcium acetate and at least about 25 grams of magnesium oxide per dose. Two doses were administered to each cow on the first (day of calving) and the second day, and one dose thereafter for days 3, 4 and 5. Serum calcium and phosphorus levels were measured each day, and the average serum and calcium levels are reported in the following table, these cows being designated "history plus treatment".

| | Calcium mg/dl | | | | | Phosphorus mg/dl | | | | |
| | Day | | | | | Day | | | | |
| Cow | 1 | 2 | 3 | 4 | 5 | 1 | 2 | 3 | 4 | 5 |
| No History, No Treatment: | 7.4 | 7.1 | 7.9 | 8.7 | 8.5 | 5.2 | 5.5 | 6.3 | 7.6 | 7.5 |
| History Plus Treatment: | 6.4 | 6.6 | 7.3 | 7.8 | 8.3 | 3.7 | 4.1 | 5.0 | 5.7 | 5.3 |

As expected, the cows having a history of milk fever exhibited initially a depressed serum calcium level, but this level increased during the 5-day treatment period and complications due to milk fever were thus avoided. One of the cows with a history of milk fever required a single intravenous calcium treatment.

EXAMPLE III

A series of cows, identified below, each having a history of milk fever, were drenched with dosages of compositions of the invention. Each dose comprised 150 grams of calcium acetate and 50 grams of magnesium acetate. Serum calcium and phosphorus levels were determined at the time of administration of the first dosage, and thereafter as indicated below, the calcium and phosphorus levels being reported in milligrams/deciliter. In each example, day 1 is the day of calving.

A. A holstein cow having a history of milk fever had a third calf at 2:00 P.M. on day 1. Dosages were administered as reported below, and no symptoms of milk fever were observed.

TABLE A

| Day | Time Sampled | Doses | Ca | P |
|---|---|---|---|---|
| 1 | 5:30 PM | 2 | 10.4 | 6.1 |
| 2 | 7:00 AM | 2 | 10.4 | 6.3 |
| 2 | 7:00 PM | 2 | 10.4 | 7.2 |
| 3 | 8:30 AM | 0 | 10.7 | 7.9 |
| 3 | 6:30 PM | 1 | 9.5 | 7.3 |
| 4 | 8:00 PM | 1 | 8.4 | 7.0 |
| 5 | 7:00 PM | 0 | 8.7 | 6.0 |

B. A holstein cow with a history of milk fever calved (5th calf) at 4:00 PM. The cow was treated with antibiotics for mastitis on the third and fourth days but received no other treatments. No symptoms of milk fever were observed.

TABLE B

| Day | Time Sampled | Doses | Ca | P |
|---|---|---|---|---|
| 1 | 5:00 PM | 2 | 7.0 | 2.2 |
| 2 | 7:00 AM | 2 | 7.0 | 3.7 |
| 2 | 7:30 PM | 2 | 8.0 | 2.9 |
| 3 | 9:00 AM | 0 | 7.7 | 5.0 |
| 3 | 6:00 PM | 1 | 6.3 | 2.7 |
| 4 | 3:30 PM | 1 | 5.7 | 3.8 |
| 5 | 5:30 PM | 0 | 6.8 | 4.2 |

C. A holstein cow with a history of milk fever calved (third calf) at 1:30 PM. No additional treatments were needed, and symptoms of milk fever did not develop.

TABLE C

| Day | Time Sampled | Doses | Ca | P |
|---|---|---|---|---|
| 1 | 2:30 PM | 2 | 6.7 | 4.0 |
| 1 | 7:00 PM | 1 | 8.3 | 4.8 |
| 2 | 8:30 PM | 2 | 9.1 | 6.2 |
| 2 | 6:30 PM | 1 | 8.9 | 5.6 |
| 3 | 7:00 PM | 1 | 6.5 | 7.1 |
| 4 | 7:30 PM | 1 | 5.7 | 5.8 |
| 5 | 7:00 PM | 0 | 7.2 | 6.6 |

D. A holstein believed to have developed milk fever during the last calving calved (fourth calf) at 1:00 PM. No additional treatments were given and no symptoms of milk fever developed.

TABLE D

| Day | Time Sampled | Doses | Ca | P |
|---|---|---|---|---|
| 1 | 5:30 PM | 2 | 6.5 | 3.2 |
| 2 | 7:00 AM | 2 | 6.4 | 4.3 |
| 2 | 6:30 PM | 2 | 5.6 | 3.4 |
| 3 | 7:00 AM | 0 | 5.8 | 4.8 |
| 3 | 5:30 PM | 1 | 4.6 | 8.3 |
| 4 | 7:00 AM | 1 | 5.5 | 7.8 |
| 5 | 7:00 AM | 0 | 6.7 | 7.2 |

E. A holstein treated for milk fever during the most recent calving calved (fourth calf) at 9:00 AM. No additional treatments were provided, and no symptoms of milk fever developed.

TABLE E

| Day | Time Sampled | Doses | Ca | P |
|---|---|---|---|---|
| 1 | 2:00 PM | 2 | 6.2 | 2.8 |
| 2 | 7:00 AM | 1.5 | 5.4 | 1.8 |
| 2 | 5:30 PM | 2 | 5.4 | 2.0 |

TABLE E-continued

| Day | Time Sampled | Doses | Ca | P |
|---|---|---|---|---|
| 3 | 7:00 AM | 1 | 6.2 | 2.2 |
| 3 | 5:30 PM | 0 | 6.8 | 3.3 |
| 4 | 7:00 AM | 1 | 7.6 | 4.3 |
| 5 | 7:00 AM | 0 | 7.7 | 6.0 |

F. A holstein cow, treated for milk fever on her last (third) calving, calved at 11:00 AM. On the evening of the next day, the cow would not eat. A toxic uterus was diagnosed, and the cow was treated with antibiotics and anti-inflammatory drugs. She resumed eating the next (third) day and did well after that. The dosages administered to this cow, as reported in the following table, each included 20,000 units of vitamin D$_3$.

TABLE F

| Day | Time Sampled | Doses | Ca | P |
|---|---|---|---|---|
| 1 | 4:00 PM | 2 | 6.8 | 6.2 |
| 2 | 7:00 AM | 2 | 6.5 | 5.5 |
| 2 | 5:30 PM | 2 | 5.2 | 2.6 |
| 3 | 7:00 AM | 2 | 5.7 | 7.4 |
| 3 | 5:30 PM | 2 | 5.9 | 5.2 |
| 4 | 7:00 AM | 2 | 6.7 | 7.2 |

G. A jersey cow, treated for milk fever on her last (third) calving, calved at 9:30 PM. No additional treatments were required and no symptoms of milk fever were observed. Each dose administered to this cow included 20,000 USP units of vitamin D$_3$.

TABLE G

| Day | Time Sampled | Doses | Ca | P |
|---|---|---|---|---|
| 1 | 9:30 PM | 2 | 5.2 | 3.5 |
| 2 | 7:00 AM | 2 | 9.3 | 4.9 |
| 2 | 6:00 PM | 2 | 8.5 | 4.7 |
| 3 | 8:00 AM | 2 | 7.3 | 4.5 |
| 3 | 6:00 PM | 2 | 8.7 | 4.8 |
| 5 | 6:00 PM | 2 | 7.0 | 3.7 |

While a preferred embodiment of the present invention has been described, it should be understood that various changes, adaptations and modifications may be made therein without departing from the spirit of the invention and the scope of the appended claims.

What is claimed is:

1. Method for reducing the propensity of a dairy cow to develop severe milk fever upon calving, comprising orally administering to the cow immediately after calving and also at least from about every 8 to 16 hours thereafter a dosage comprising an effective quantity of a water-soluble calcium salt and an affective quantity of complexing agent capable of complexing serum phosphorus to form a water-insoluble phosphorous complex, and providing magnesium or equivalent metal and wherein the first such dosage provides at least about 17 grams of magnesium or its equivalent, said administration continuing for at least three consecutive dosages within about the first 30 hours after calving.

2. The method of claim 1 in which the water-soluble calcium compound is administered in a quantity providing, within the first 24 hours after calving, at least about 75 grams of calcium.

3. The method of claim 1 in which the complexing agent is administered in a quantity providing, within the first 24 hours after calving, at least about 17 grams of magnesium or equivalent metal.

4. The method of claim 1 in which said administration is continued for at least six consecutive dosages.

5. The method of claim 1 in which said dosage administered immediately after calving is sufficient to provide at least about 75 grams of calcium in the form of the water-soluble calcium salt.

6. The method of claim 5 wherein the fourth dosage provides calcium in the form of the water-soluble calcium compound, in an amount not exceeding about 40 grams.

7. The method of claim 5 in which the quantity of complexing agent provided to the cow in the fourth dosage is not greater than about 8 grams of magnesium or its equivalent.

8. The method of claim 1 wherein the water-soluble calcium compound is the calcium salt of an organic acid.

9. The method of claim 8 in which the calcium salt is calcium acetate or calcium propionate.

10. The method of claim 1 in which the water-soluble calcium compound is calcium acetate and in which the complexing agent comprises magnesium acetate, magnesium oxide, magnesium sulfate or mixtures thereof.

11. The method of any of claim 1 through 7 in which the calcium compound is calcium acetate and the complexing agent comprises magnesium sulfate and magnesium oxide.

12. Method for reducing the propensity of a dairy cow to develop severe milk fever upon calving, comprising orally administering to the cow immediately after calving, and also from at least about every 8 to 16 hours thereafter, a dosage in water comprising at least about 150 grams of calcium acetate and a sufficient quantity of one or more magnesium compounds comprising magnesium sulfate or magnesium oxide, or both, in an amount providing at least about 8 grams of magnesium, said administration continuing for at least three dosages.

13. The method of claim 12 in which the dosage administered to the cow immediately after calving comprises at least 300 grams of calcium acetate and sufficient magnesium compounds to provide at least 17 grams of magnesium.

14. The method of claim 1 or claim 12 in which the dosages include at least 20,000 units of Vitamin $D_3$.

15. A milk fever prophylactic composition orally administerable to a milk cow immediately after calving and also from about every 8 to about 16 hours thereafter for a total of at least three such administrations in about the first 30 hours following calving, the composition comprising a water-soluble calcium salt providing at least about 40 grams of calcium, and a complexing agent capable of reacting with serum phosphorus to form a generally water-insoluble phosphorous complex and providing at least about 8 grams of magnesium or its equivalent.

16. A milk fever prophylactic composition orally administerable to a dairy cow, the composition comprising at least about 150 grams of a water-soluble calcium salt of an organic acid, and at least one magnesium compound comprising magnesium sulfate, magnesium oxide, or magnesium acetate in an amount providing at least about 8 grams of magnesium.

17. The prophylactic composition of claim 16 in which said composition includes at least about 300 grams of said calcium salt, and sufficient magnesium compound to provide at least about 17 grams of magnesium.

18. The prophylactic composition of claim 16 wherein the composition includes at least 20,000 USP units of Vitamin $D_3$.

19. A unit medicinal dosage to be administered to a dairy cow immediately after calving and also from about every 8 to 16 hours thereafter for at least three dosages given within 30 hours of calving to reduce the propensity of the cow to develop severe milk fever, the unit dosage comprising, in water-soluble powdered form, a mixture of at least about 300 grams of calcium acetate and at least about 100 grams of a composition comprising one or more of magnesium acetate, magnesium oxide and magnesium sulfate.

20. The unit dosage of claim 19 including at least about 20,000 USP units of Vitamin $D_3$.

21. Method for reducing the propensity of a dairy cow to develop severe milk fever upon calving, comprising orally administering to the cow immediately after calving and also at least from about every 8 to 16 hours thereafter a dosage comprising an effective quantity of a water-soluble calcium salt of a monobasic acid and an effective quantity of a serum phosphorus-complexing agent selected from the group consisting of the oxides, hydroxides and salts of magnesium, iron, manganese, zinc, aluminum, and chromium, said administration continuing for at least three consecutive doses within about the first 30 hours after calving.

22. Method for reducing the propensity of a dairy cow to develop severe milk fever upon calving, comprising orally administering to the cow immediately after calving and also at least from about every 8 to 16 hours thereafter a dosage comprising an effective quantity of a water-soluble calcium compound selected from the group consisting of calcium acetate, calcium propionate, calcium chloride, calcium citrate, and calcium borogluconate, and an effective quantity of a serum phosphorus complexing agent selected from the group consisting of the oxides, hydroxides and salts of magnesium, iron, manganese, zinc, aluminum, and chromium, said administration continuing for at least three consecutive dosages within about the first 30 hours after calving.

23. The method of claim 22 wherein the serum phosphorus-complexing agent is magnesium acetate, magnesium oxide, magnesium sulfate or mixtures thereof.

24. Method for reducing the propensity of a dairy cow to develop severe milk fever upon calving, comprising orally administering to the cow immediately after calving and also at least from about every 8 to 16 hours thereafter a dosage comprising an effective quantity of calcium acetate and an effective quantity of a serum phosphorus complexing agent selected from the group consisting of magnesium acetate, magnesium oxide, magnesium sulfate or mixtures thereof, said administration continuing for at least three consecutive dosages within about the first 30 hours after calving.

* * * * *